US008610576B2

(12) United States Patent
Sweeney et al.

(10) Patent No.: US 8,610,576 B2
(45) Date of Patent: *Dec. 17, 2013

(54) ROUTING COMMUNICATIONS TO A PERSON WITHIN A FACILITY

(75) Inventors: Jeffrey Michael Sweeney, Olathe, KS (US); Kelsyn Donel Seven Rooks, Sr., Overland Park, KS (US); Michael Clayton Robinson, Overland Park, KS (US)

(73) Assignee: CenturyLink Intellectual Property LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/537,514

(22) Filed: Jun. 29, 2012

(65) Prior Publication Data

US 2012/0274464 A1   Nov. 1, 2012

Related U.S. Application Data

(63) Continuation of application No. 12/112,738, filed on Apr. 30, 2008, now Pat. No. 8,237,551.

(51) Int. Cl.
    *G08B 5/22*   (2006.01)
(52) U.S. Cl.
    USPC .............. 340/572.1; 340/286.07; 340/539.12; 340/573.1; 379/106.02; 379/114.28; 379/126; 379/201.1; 455/404.2; 455/406; 705/2
(58) Field of Classification Search
    USPC ................. 340/286.07, 539.12, 572.1, 573.1; 379/106.02, 114.28, 126, 201.1; 455/404.2, 406; 705/2
    See application file for complete search history.

(56) References Cited

U.S. PATENT DOCUMENTS

| | | |
|---|---|---|
| 3,703,714 A | 11/1972 | Andrews |
| 3,997,718 A | 12/1976 | Ricketts et al. |
| 4,103,337 A | 7/1978 | Whiteside |
| 4,303,937 A | 12/1981 | Cook |
| 4,375,637 A | 3/1983 | Desjardins |
| 4,656,656 A | 4/1987 | Mundy et al. |
| 4,866,515 A | 9/1989 | Tagawa et al. |
| 4,872,195 A | 10/1989 | Leonard |
| 4,959,713 A | 9/1990 | Morotomi et al. |
| 4,992,866 A | 2/1991 | Morgan |
| 5,027,211 A | 6/1991 | Robertson |
| 5,061,916 A | 10/1991 | French et al. |
| 5,086,385 A | 2/1992 | Launey |

(Continued)

FOREIGN PATENT DOCUMENTS

| | | |
|---|---|---|
| EP | 1 445 917 | 8/2004 |
| JP | 2002-002486 | 1/2002 |

OTHER PUBLICATIONS

TrueCom Building Communications Systems Communications Controllers 5120 Series, May 1998, Publication S5120-0012-7, pp. 1-6.

(Continued)

*Primary Examiner* — Brent Swarthout
(74) *Attorney, Agent, or Firm* — Swanson & Bratschun, L.L.C.

(57) ABSTRACT

A system and method for tracking a person at a facility to enable communications. A presence of the person is detected at a location at the facility. Communications intended for the person are associated with the location. The communications are routed to the person at that location.

20 Claims, 6 Drawing Sheets

(56) References Cited

U.S. PATENT DOCUMENTS

| | | |
|---|---|---|
| 5,109,222 A | 4/1992 | Welty |
| 5,172,413 A | 12/1992 | Bradley et al. |
| 5,187,735 A | 2/1993 | Garcia et al. |
| 5,310,349 A | 5/1994 | Daniels et al. |
| 5,479,267 A | 12/1995 | Hashimoto |
| 5,550,863 A | 8/1996 | Yurt et al. |
| 5,565,908 A | 10/1996 | Ahmad |
| 5,585,838 A | 12/1996 | Lawler et al. |
| 5,594,786 A * | 1/1997 | Chaco et al. ............... 379/93.09 |
| 5,601,432 A | 2/1997 | Bergman |
| 5,621,456 A | 4/1997 | Florin et al. |
| 5,684,952 A | 11/1997 | Stein |
| 5,689,242 A | 11/1997 | Sims et al. |
| 5,790,176 A | 8/1998 | Craig |
| 5,790,935 A | 8/1998 | Payton |
| 5,940,594 A | 8/1999 | Ali et al. |
| 6,005,927 A | 12/1999 | Rahrer et al. |
| 6,020,881 A | 2/2000 | Naughton et al. |
| 6,038,425 A | 3/2000 | Jeffrey |
| 6,049,823 A | 4/2000 | Hwang |
| 6,060,994 A | 5/2000 | Chen |
| 6,072,395 A | 6/2000 | Vega |
| 6,149,441 A | 11/2000 | Pellegrino et al. |
| 6,182,128 B1 | 1/2001 | Kelkar et al. |
| 6,185,773 B1 | 2/2001 | Goedde |
| 6,192,282 B1 | 2/2001 | Smith et al. |
| 6,233,428 B1 | 5/2001 | Fryer |
| 6,240,410 B1 | 5/2001 | Wical |
| 6,243,459 B1 | 6/2001 | Cannon et al. |
| 6,370,323 B1 | 4/2002 | Adolph et al. |
| 6,374,079 B1 | 4/2002 | Hsu |
| 6,438,596 B1 | 8/2002 | Ueno et al. |
| 6,501,502 B1 | 12/2002 | Chen |
| 6,507,726 B1 | 1/2003 | Atkinson et al. |
| 6,561,812 B1 | 5/2003 | Burmester et al. |
| 6,603,847 B1 | 8/2003 | Griffith |
| 6,661,340 B1 | 12/2003 | Saylor et al. |
| 6,731,746 B1 | 5/2004 | Usami |
| 6,748,597 B1 | 6/2004 | Frisco et al. |
| 6,760,431 B1 | 7/2004 | Haimi-Cohen |
| 6,769,127 B1 | 7/2004 | Bonomi et al. |
| 6,775,518 B2 | 8/2004 | Norcott et al. |
| 6,813,777 B1 | 11/2004 | Weinberger et al. |
| 6,844,807 B2 | 1/2005 | Inoue et al. |
| 6,879,243 B1 | 4/2005 | Booth et al. |
| 6,914,977 B2 | 7/2005 | Danner et al. |
| 6,925,499 B1 | 8/2005 | Chen et al. |
| 6,970,183 B1 | 11/2005 | Monroe |
| 6,975,346 B2 | 12/2005 | Kumhyr |
| 7,028,096 B1 | 4/2006 | Lee |
| 7,035,390 B2 | 4/2006 | Elliott |
| 7,046,689 B2 | 5/2006 | Burns et al. |
| 7,123,142 B2 | 10/2006 | Bohbot et al. |
| 7,159,233 B2 | 1/2007 | Son et al. |
| 7,185,282 B1 | 2/2007 | Naidoo et al. |
| 7,246,369 B1 | 7/2007 | Duan et al. |
| 7,310,317 B2 | 12/2007 | Yepez et al. |
| 7,426,197 B2 * | 9/2008 | Schotten et al. ............... 370/328 |
| 7,697,503 B2 | 4/2010 | Frederick |
| 7,697,927 B1 | 4/2010 | Owens |
| 7,714,728 B2 | 5/2010 | Koblasz |
| 7,765,573 B1 | 7/2010 | Owens |
| 7,786,891 B2 | 8/2010 | Owens |
| 8,237,551 B2 * | 8/2012 | Sweeney et al. ......... 340/286.07 |
| 2002/0033760 A1 | 3/2002 | Kobayashi |
| 2002/0038461 A1 | 3/2002 | White et al. |
| 2002/0044642 A1 | 4/2002 | Danner et al. |
| 2002/0048224 A1 | 4/2002 | Dygert et al. |
| 2002/0049977 A1 | 4/2002 | Miller et al. |
| 2002/0112121 A1 | 8/2002 | Gerszberg et al. |
| 2002/0124258 A1 | 9/2002 | Fritsch |
| 2002/0138842 A1 | 9/2002 | Chong et al. |
| 2002/0164155 A1 | 11/2002 | Mate |
| 2002/0166123 A1 | 11/2002 | Schrader et al. |
| 2002/0170064 A1 | 11/2002 | Monroe et al. |
| 2002/0180579 A1 | 12/2002 | Nagaoka et al. |
| 2003/0009668 A1 | 1/2003 | Chan et al. |
| 2003/0046369 A1 | 3/2003 | Sim et al. |
| 2003/0050935 A1 | 3/2003 | Spetsmann |
| 2003/0051239 A1 | 3/2003 | Hudspeth |
| 2003/0052787 A1 * | 3/2003 | Zerhusen et al. .......... 340/573.1 |
| 2003/0105854 A1 | 6/2003 | Thorsteinsson et al. |
| 2003/0121050 A1 | 6/2003 | Kalva et al. |
| 2003/0123450 A1 | 7/2003 | Wright et al. |
| 2003/0182420 A1 | 9/2003 | Jones et al. |
| 2003/0191802 A1 | 10/2003 | Zhao et al. |
| 2003/0200009 A1 | 10/2003 | Von Kannewurff et al. |
| 2003/0204856 A1 | 10/2003 | Buxton |
| 2003/0208762 A1 | 11/2003 | Hanai et al. |
| 2004/0003051 A1 | 1/2004 | Krzyzanowski et al. |
| 2004/0015993 A1 | 1/2004 | Yacenda et al. |
| 2004/0039757 A1 | 2/2004 | McClure |
| 2004/0049789 A1 | 3/2004 | Bower et al. |
| 2004/0066931 A1 | 4/2004 | Tankhiwale |
| 2004/0117638 A1 | 6/2004 | Monroe |
| 2004/0117647 A1 | 6/2004 | Ballard |
| 2004/0148632 A1 | 7/2004 | Park et al. |
| 2004/0172658 A1 | 9/2004 | Rakib et al. |
| 2004/0194148 A1 | 9/2004 | Schultz et al. |
| 2004/0210944 A1 | 10/2004 | Brassil et al. |
| 2004/0253945 A1 | 12/2004 | Janik |
| 2004/0268410 A1 | 12/2004 | Barton et al. |
| 2005/0003338 A1 | 1/2005 | Norcott |
| 2005/0028208 A1 | 2/2005 | Ellis et al. |
| 2005/0044166 A1 | 2/2005 | Colville et al. |
| 2005/0078934 A1 | 4/2005 | Fish et al. |
| 2005/0080818 A1 | 4/2005 | Kindberg et al. |
| 2005/0125083 A1 | 6/2005 | Kiko |
| 2005/0131957 A1 | 6/2005 | Watkinson |
| 2005/0177853 A1 | 8/2005 | Williams et al. |
| 2005/0193098 A1 | 9/2005 | Khandpur et al. |
| 2005/0206513 A1 | 9/2005 | Fallon |
| 2005/0215244 A1 | 9/2005 | Whitson |
| 2005/0254440 A1 | 11/2005 | Sorrell |
| 2005/0278773 A1 | 12/2005 | DeCinQue et al. |
| 2006/0004606 A1 * | 1/2006 | Wendl et al. ..................... 705/2 |
| 2006/0005224 A1 | 1/2006 | Dunning et al. |
| 2006/0020993 A1 | 1/2006 | Hannum et al. |
| 2006/0069736 A1 | 3/2006 | Czeisler et al. |
| 2006/0085824 A1 | 4/2006 | Bruck et al. |
| 2006/0088806 A1 | 4/2006 | Quinn |
| 2006/0220798 A1 | 10/2006 | Willis |
| 2007/0006276 A1 | 1/2007 | Ashley et al. |
| 2007/0050828 A1 | 3/2007 | Renzi et al. |
| 2007/0094045 A1 * | 4/2007 | Cobbs et al. ..................... 705/2 |
| 2007/0130590 A1 | 6/2007 | Nash-Putnam |
| 2007/0241901 A1 * | 10/2007 | Cage et al. ................. 340/572.1 |
| 2008/0016545 A1 | 1/2008 | DeCinQue et al. |
| 2008/0092168 A1 | 4/2008 | Logan et al. |
| 2008/0233969 A1 * | 9/2008 | Mergen ..................... 455/456.1 |
| 2008/0249376 A1 * | 10/2008 | Zaleski ..................... 600/301 |
| 2010/0141391 A1 | 6/2010 | Music et al. |
| 2012/0214454 A1 | 8/2012 | Frederick |

OTHER PUBLICATIONS

Advancements Bring Windows-based Software, Ethernet Network Compatibility to 5120 Intercom Systems, Feb. 2001, pp. 1-2.
Sprint TekNet IP Installation Manual, Oct. 2001, 60 pages.
Sprint TekNet IP Integrated Communications System, Installation Overview, Jul. 19, 2002, 48 pages.
Spint TekNet IP Overview press release, Jul. 18, 2003, 2 pages.
Sprint TekNet IP for Higher Education press release, Jul. 18, 2003, 5 pages.
System Integrates All School Tech Functions press release, Jul. 18, 2003, 1 page.
IC-Net Systems—RF Coax Network, ICC-Smart TV Controllers Feb. 17, 2004, 5 pages.
Non-Final Office Action dated Nov. 16, 2006 for U.S. Appl. No. 10/928,568, 14 pages.
Response filed Jan. 8, 2008 to Non-Final Office Action dated Oct. 10, 2007 for U.S. Appl. No. 10/928,568, 10 pages.
Response filed Feb. 21, 2007 to Non-Final Office Action dated Nov. 16, 2006 for U.S. Appl. No. 10/928,568, 7 pages.

(56) References Cited

OTHER PUBLICATIONS

Non-Final Office Action dated Mar. 23, 2007 for U.S. Appl. No. 10/236,286.
Final Office Action dated May 21, 2007 for U.S. Appl. No. 10/928,568, 10 pages.
U.S. Appl. No. 11/303,437, Notice of Publication dated Jun. 21, 2007, 1 page.
Response filed Jul. 20, 2007 to Final Office Action dated May 21, 2007 for U.S. Appl. No. 10/928,568, 10 pages.
Response filed Jul. 23, 2007 to Non-Final Office Action dated Mar. 23, 2007 for U.S. Appl. No. 10/236,286.
Non-Final Office Action dated Oct. 10, 2007 for U.S. Appl. No. 10/928,568, 12 pages.
Final Office Action dated Oct. 16, 2007 for U.S. Appl. No. 10/236,286.
Non-Final Office Action dated Oct. 18, 2007 for U.S. Appl. No. 11/042,263, 12 pages.
Response filed Oct. 26, 2007 to Final Office Action dated Oct. 16, 2007 for U.S. Appl. No. 10/236,286.
Advisory Action dated Nov. 19, 2007 for U.S. Appl. No. 10/236,286.
Non-Final Office Action dated Dec. 11, 2007 for U.S. Appl. No. 10/803,046, 11 pages.
Response filed Jan. 18, 2008 Non-Final Office Action dated Oct. 18, 2007 for U.S. Appl. No. 11/042,263, 10 pages.
Non-Final Office Action dated Feb. 13, 2008 for U.S. Appl. No. 10/236,286.
Response filed Mar. 11, 2008 to Non-Final Office Action dated Dec. 11, 2007 for U.S. Appl. No. 10/803,046, 8 pages.
Final Office Action dated Apr. 18, 2008 for U.S. Appl. No. 11/042,263, 17 pages.
Final Office Action dated Apr. 28, 2008 for U.S. Appl. No. 10/928,568, 16 pages.
Response filed May 13, 2008 to Non-Final Office Action dated Feb. 13, 2008 for U.S. Appl. No. 10/236,286.
Final Office Action dated Jun. 3, 2008 for U.S. Appl. No. 10/803,046, 10 pages.
RCE and Response filed Jun. 30, 2008 to Final Office Action dated Apr. 28, 2008 for U.S. Appl. No. 10/928,568, 12 pages.
RCE and Response filed Jul. 18, 2008 Final Office Action dated Apr. 18, 2008 for U.S. Appl. No. 11/042,263, 11 pages.
Advisory Action date mailed Jul. 28, 2008 for U.S. Appl. No. 10/928,568, 4 pages.
Non-Final Office Action dated Aug. 1, 2008 for U.S. Appl. No. 11/074,861, 14 pages.
Non-Final Office Action dated Aug. 21, 2008 for U.S. Appl. No. 11/042,263, 18 pages.
Response filed Sep. 3, 2008 to Final Office Action dated Jun. 3, 2008 for U.S. Appl. No. 10/803,046, 8 pages.
Final Office Action dated Sep. 10, 2008 for U.S. Appl. No. 10/236,286.
RCE/Response filed Oct. 28, 2008 to Final Office Action date mailed Apr. 28, 2008 for U.S. Appl. No. 10/928,568, 5 pages.
Response filed Nov. 3, 2008 to Non-Final Office Action dated Aug. 1, 2008 for U.S. Appl. No. 11/074,861, 8 pages.
Non-Final Office Action date mailed Nov. 10, 2008 for U.S. Appl. No. 10/951,740, 13 pages.
Response filed Nov. 21, 2008 Non-Final Office Action dated Aug. 21, 2008 for U.S. Appl. No. 11/042,263, 11 pages.
Non-Final Office Action date mailed Dec. 11, 2008 for U.S. Appl. No. 10/803,046, 11 pages.
Non-Final Office Action dated Nov. 10, 2008 in U.S. Appl. No. 10/951,740, 13 pages.
Final Office Action date mailed Jan. 7, 2009 for U.S. Appl. No. 11/074,861, 15 pages.
U.S. Appl. No. 11/303,437, Office Action dated Jan. 7, 2009, 14 pages.
Non-Final Office Action date mailed Jan. 9, 2009 for U.S. Appl. No. 10/928,568, 6 pages.
Non-Final Office Action date mailed Jan. 21, 2009 for U.S. Appl. No. 10/694,337.

Response filed Feb. 10, 2009 to Non-Final Office Action date mailed Nov. 10, 2008 for U.S. Appl. No. 10/951,740, 8 pages.
RCE/Amendment filed Feb. 27, 2009 to Final Action dated Jan. 7, 2009 in U.S. Appl. No. 11/074,861, 10 pages.
Final Rejection date mailed Mar. 4, 2009 in U.S. Appl. No. 11/042,263, 18 pages.
Response filed Mar. 11, 2009 to Non-Final Action dated Dec. 11, 2008 in U.S. Appl. No. 10/951,740, 8 pages.
Response filed Mar. 18, 2009 to Non-Final Action dated Jan. 21, 2009 in U.S. Appl. No. 10/694,337.
Non-Final Rejection date mailed Mar. 23, 2009 in U.S. Appl. No. 11/074,861, 18 pages.
Non-Final Rejection date mailed Apr. 2, 2009 in U.S. Appl. No. 11/897,439.
Response filed Apr. 9, 2009 to Non-Final Action date mailed Jan. 29, 2009 in U.S. Appl. No. 10/928,568, 5 pages.
Pre-Appeal Request for Review and Remarks to same; Notice of Appeal all filed on Apr. 10, 2009 in U.S. Appl. No. 11/042,263, 11 pages.
Response filed Apr. 16, 2009 to Non-Final Action date mailed Apr. 2, 2009 in U.S. Appl. No. 11/897,439.
Response filed Apr. 16, 2009 to Non-Final Rejection date mailed Mar. 23, 2009 in U.S. Appl. No. 11/074,861, 11 pages.
Final Rejection date mailed Jun. 10, 2009 in U.S. Appl. No. 11/074,861, 19 pages.
Final Rejection date mailed Jun. 18, 2009 in U.S. Appl. No. 10/694,337.
Final Rejection date mailed Jun. 19, 2009 in U.S. Appl. No. 10/951,740, 15 pages.
U.S. Appl. No. 11/303,437, Final Office Action dated Jul. 8, 2009, 19 pages.
Final Rejection date mailed Jul. 14, 2009 in U.S. Appl. No. 11/897,439, 14 pages.
Final Rejection date mailed Jul. 30, 2009 in U.S. Appl. No. 10/928,568, 7 pages.
Response filed Aug. 4, 2009 to Final Rejection dated Jul. 14, 2009 in U.S. Appl. No. 11/897,439, 9 pages.
Response filed Aug. 10, 2009 to Final Action dated Jun. 10, 2009 in U.S. Appl. No. 11/074,861, 13 pages.
Response filed Aug. 13, 2009 to Final Rejection dated Jun. 18, 2009 in U.S. Appl. No. 10/694,337.
Advisory Action date mailed Aug. 26, 2009 in U.S. Appl. No. 11/074,861, 3 pages.
Advisory Action date mailed Aug. 31, 2009 in U.S. Appl. No. 10/694,337.
RCE/Amendment filed Sep. 1, 2009 to Final Rejection dated Jun. 19, 2009 in U.S. Appl. No. 10/951,740, 11 pages.
Pre-Brief Appeal Conference Decision date mailed Sep. 8, 2009 in U.S. Appl. No. 11/042,263, 2 pages.
RCE/Amendment filed Sep. 8, 2009 in U.S. Appl. No. 11/074,861, 16 pages.
Advisory Action date mailed Sep. 18, 2009 in U.S. Appl. No. 11/897,439, 3 pages.
Pre-Appeal Brief Request for Review and Remarks to same; Notice of Appeal all filed on Sep. 18, 2009 in U.S. Appl. No. 10/694,337.
RCE/Amendment filed Oct. 5, 2009 in U.S. Appl. No. 11/897,439, 10 pages.
Non-Final Rejection date mailed Oct. 14, 2009 in U.S. Appl. No. 11/074,861, 24 pages.
Non-Final Rejection date mailed Oct. 15, 2009 in U.S. Appl. No. 10/951,740, 17 pages.
Pre-Appeal Conference Decision date mailed Nov. 18, 2009 in U.S. Appl. No. 10/694,337.
U.S. Appl. No. 11/303,437, Notice of Allowance dated Dec. 1, 2009, 4 pages.
Notice of Allowance and Fees Due date mailed Dec. 7, 2009 in U.S. Appl. No. 11/042,263, 11 pages.
Non-Final Rejection date mailed Dec. 16, 2009 in U.S. Appl. No. 11/897,439, 14 pages.
RCE/Amendment filed Dec. 16, 2009 in U.S. Appl. No. 10/694,337.
Amendment filed Jan. 13, 2010 to Non-Final Rejection dated Oct. 14, 2009 in U.S. Appl. No. 11/074,861, 11 pages.

(56) References Cited

OTHER PUBLICATIONS

Examiner Interview Summary date mailed Jan. 13, 2010 in U.S. Appl. No. 11/074,861, 11 pages.
Response filed Jan. 15, 2010 to Non-Final Rejection date mailed Oct. 15, 2009 in U.S. Appl. No. 10/951,740, 10 pages.
Non-Final Rejection date mailed Jan. 20, 2010 in U.S. Appl. No. 10/694,337.
Non-Final Rejection date mailed Feb. 22, 2010 in U.S. Appl. No. 10/803,046, 11 pages.
Response filed Feb. 26, 2010 to Non-Final Rejection date mailed Jan. 20, 2010 in U.S. Appl. No. 10/694,337.
Reply filed Mar. 3, 2010 to Non-Final Rejection date mailed Dec. 16, 2010 in U.S. Appl. No. 11/897,439, 9 pages.
Examiner Interview Summary date mailed Mar. 5, 2010 in U.S. Appl. No. 10/694,337.
U.S. Appl. No. 11/303,437, Issue Notification dated Mar. 24, 2010, 1 page.
Final Rejection date mailed May 11, 2010 in U.S. Appl. No. 10/694,337.
U.S. Appl. No. 12/112,738; Non-Final Rejection dated Jun. 1, 2010, 7 pages.
Notice of Allowance date mailed Jun. 15, 2010 in U.S. Appl. No. 11/897,439, 4 pages.
Response filed Jun. 17, 2010 to Non-final Office Action date mailed Feb. 22, 2010 in U.S. Appl. No. 10/803,046, 16 pages.
Supplemental Notice of Allowability date mailed Jul. 22, 2010 in U.S. Appl. No. 11/897,439, 2 pages.
Notice of Allowance date mailed Aug. 5, 2010 in U.S. Appl. No. 10/951,740, 4 pages.
U.S. Appl. No. 12/112,738; Final Rejection dated Nov. 3, 2010, 8 pages.
U.S. Appl. No. 12/112,738; Non-Final Rejection dated Feb. 28, 2011, 7 pages.
U.S. Appl. No. 12/112,738; Final Rejection dated Aug. 8, 2011, 8 pages.
U.S. Appl. No. 12/715,670; Notice of Allowance dated Feb. 2, 2012; 14 pages.
U.S. Appl. No. 12/112,738; Notice of Allowance dated Mar. 29, 2012, 5 pages.
U.S. Appl. No. 12/715,670; Issue Notification dated May 9, 2012; 1 page.
U.S. Appl. No. 12/112,738; Issue Notification dated Jul. 18, 2012; 1 page.
U.S. Appl. No. 13/461,344; Non-Final Office Action dated Aug. 30, 2012; 31 pages.

\* cited by examiner

FIG. 6

| | | | |
|---|---|---|---|
| | | Billing Invoice | 600 |

602 ✓ Doe, Janice
604 Invoice: 6/21/10 – 6/24/10
606 ☐ Billed to credit card ending in 0451
    ☐ Bill sent to client Charges 608:
- ☐ Movie-on-demand: I still know what you did last summer when you made me deaf screaming in my ear: II  (Delivery room) — 5.99
- ☐ Pay-per-view: Ultimate cage fighters in costume  (Recovery room) — 19.99
- ☐ Internet usage: 180 minutes * .03  (Delivery and recovery room) — 10.80
- ☐ Email/Text messages sent and received: 12 messages * .15 — 1.80
- ☐ Outgoing phone calls: 115 minutes * .10 — 11.60

610 Total:  50.18

Outgoing Phone Calls

| Party | Date | $/Mins |
|---|---|---|
| 1-214-999-9999 | 062110 | 2.50 |
| 1-214-997-9997 | 062110 | 2.80 |
| 1-214-999-1234 | 062210 | .30 |
| 1-208-999-9999 | 062310 | 4.90 |
| Local | 012309 | |
| 1-214-999-9999 | 012309 | 1.00 |
| 1-208-999-9999 | 012409 | .2 |

612

ROUTING COMMUNICATIONS TO A PERSON WITHIN A FACILITY

CROSS REFERENCE TO RELATED APPLICATION

This application is a continuation of U.S. patent application Ser. No. 12/112,738, filed Apr. 30, 2008 now U.S. Pat. No. 8,237,551 by Jeffrey Michael Sweeney, et al. and entitled, "System and Method for In-Patient Telephony," which is hereby incorporated by reference in its entirety.

BACKGROUND

The use of and development of communications has grown nearly exponentially in recent years. The growth is fueled by larger networks with more reliable protocols and better communications hardware available to service providers and consumers. Individuals have come to expect and rely on different communications mediums regardless of location or circumstances. In many cases individuals are required to go to locations where they are unable to use personal communications devices or systems.

For example, while visiting a hospital an individual may be prevented from using a personal cell phone due to sensitive medical equipment and hospital policies. As a result, the individual may be dependent on the communications systems available at the hospital. Unfortunately, it may be difficult for the individual to receive communications if he or she is moved to separate locations or rooms within the hospital. Similarly, it may be difficult for the individual to retrieve a personal communications device or payment information based on physical limitations, such as sickness, recovery from surgery or attached heart rate monitors. As a result, communicating from within such a facility may be difficult, inconvenient or impossible.

SUMMARY

One embodiment includes a system and method for tracking patients to enable communications. A presence of a patient may be detected in a room. Communications intended for the patient may be associated with the room. The communications may be routed to the patient in the room.

Another embodiment includes a server for routing communications to a patient in a medical facility. The server may include a communications interface configured to receive an input specifying a room assigned to the patient in response to a remote device detecting the presence of the patient in the room from a RFID tag. The server may also include routing logic configured to route incoming communications to one or more communications devices in the room based on the detected RFID tag. The server may also include a billing database configured to charge an account of the patient for communications made from the one or more communications devices.

Yet another embodiment includes a server configured to route communications to a user. The server may include a processor for executing a set of instructions and a memory for storing the set of instructions. The set of instructions may be configured to detect a presence of a patient in a room utilizing an identifier that is remotely scanned, modify an account of the patient to designate the room as a current location of the patient for managing communications intended for the patient, and route the communications to a device located in the room in response to modifying the account.

BRIEF DESCRIPTION OF THE DRAWINGS

Illustrative embodiments of the present invention are described in detail below with reference to the attached drawing figures, which are incorporated by reference herein and wherein:

FIG. 6 is a pictorial representation of a billing invoice in accordance with an illustrative embodiment.

DETAILED DESCRIPTION OF THE DRAWINGS

The illustrative embodiments provide a system and method for enhancing communications for a patient in a facility. In one embodiment, the facility is a hospital in which the patient visits multiple rooms as part of a stay as a patient or family member. An identifier may be associated with the patient. One or more scanners within the facility may detect the identifier indicating the presence of the patient as moves from location to location are made. Presence is the current location of a patient. As a result, incoming communications intended for the patient are routed to the current location and communications devices within the location. Similarly, the user may communicate using the communications device with all expenses charged to an account or profile associated with the user. As a result, the patient may more easily communicate regardless of the location.

Figure 1:
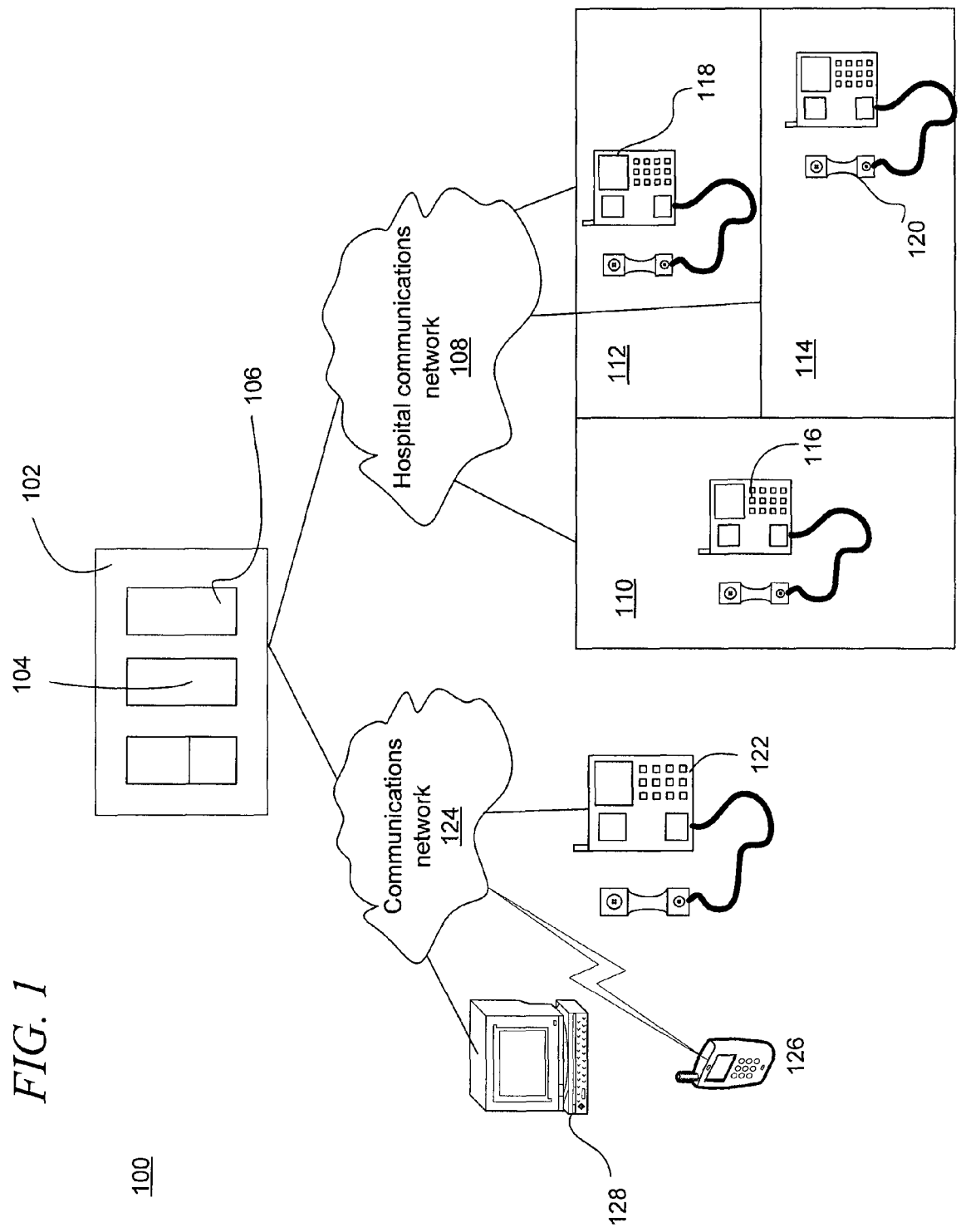
FIG. 1 is a pictorial representation of a communications system in accordance with an illustrative embodiment.

FIG. 1 is a pictorial representation of a communications system in accordance with an illustrative embodiment. The communication system 100 is one embodiment of a communications environment that may be utilized to send and receive communications. The communication system 100 may include a communications management system 102, a server 104, a billing database 106, a hospital communications network 108, locations 110, 112, and 114, VoIP phones 116, 118, 120, and 122, communications network 124, cell phone 126 and client 128.

The communications management system 102 is one or more devices utilized to enable, initiate, route, and manage communications between one or more telephonic devices. The communications management system 102 may include one or more devices networked to manage the hospital communications network 108. In one embodiment, the communications management system 102 provides an access point to the hospital communications network 124. The communications management system 102 may include any number of servers, routers, switches or advanced intelligent devices. The hospital communications network 108 and communications network 124 sends and receives electronic signals through any number of transmission mediums. For example, the hospital communications network 108 and communications network 124 may include various fiber optics, cables, transmission towers, antennas or other elements for transmitting voice communications, data, packets, and other information to the connected telecommunications devices.

The telecommunications devices as herein defined refer to devices and software configured to communicate over the hospital communications network. The telecommunications devices may include laptops, computers, voice over Internet Protocol (VoIP) phones, plain old telephone service (POTS) phones, fax machines, terminals, servers, medical equipment, televisions or other devices and applications suitable for communicating voice signals, messages, data, and other network traffic. In a preferred embodiment, the communications management system 102 and the hospital communications network 108 work to transmit voice communications to the VoIP phones 116, 118, 120. However, the hospital communications network 108 may enable POTS, wireless service or other forms of voice communications.

As shown in FIG. 1, the hospital communications network 108 enables communications for any number of telecommunications devices. The example of FIG. 1 is simplified for purposes of explaining the illustrative embodiments. In one embodiment, the hospital communications network 108 enables communications through the VoIP phones 116, 118, and 120 from the respective locations 110, 112, and 114. The locations 110, 112, and 114 may represent rooms, buildings, sections or other portions of the facility. In one ongoing example, the locations 110, 112, and 114 may represent the rooms that a patient will be assigned to during a stay at a medical facility, such as a hospital. Although the illustrative embodiments are described for a medical facility or hospital, the system and method herein described may be similarly applied to other buildings organizational structures or environments. For example, the process may apply to a work campus, a secure facility or an educational facility.

In one example, the location 110 may represent a preparation room. The location 112 may represent a delivery room for delivering a baby and the location 114 may represent a recovery and out-patient room. During a user or patient's stay at a medical facility, the patient may visit each of the locations 110, 112, and 114 for a random time period based on the circumstances of the patient. As in most medical facilities, the patient may be required to sign in or register before entering the facility or any of the locations 110, 112, and 114.

In one embodiment, the patient may be assigned an account number, profile, phone number, and medical bracelet or tag when initiating a visit to a medical facility. The account is a billing record for tracking the patient's information and expenses while in the facility and in particular, the locations 110, 112, and 114. The phone number is a virtual phone number, IP address, nickname or other information associated with the patient that may be used to call the VoIP phones 116, 118, and 120 based on the determined location of the patient. In one embodiment, a profile may be used to store the account information and any other information related to the care, management, and communications to and from the patient. The profile may store the current location of the patient as well as the locations 110, 112, and 114 previously visited by the patient so that the user may see expenses incurred in each of the locations 110, 112, and 114.

The bracelet or medical tag is one example of an identifier assigned to or attached to the patient. The identifier is a device, code or information that may be scanned or detected to indicate the presence of the patient in any of the locations 110, 112, and 114. In one embodiment, the identifier is a medical bracelet as further described in FIG. 3. The identifier provides a minimally intrusive system and method for tracking the presence of the patient through any number of locations.

The presence or current location of the patent may be tracked by the communications management system 102. In one embodiment, the server 104 may utilize logic in any number of databases to identify and record the present location of the patient. Any expenses incurred by the patient based on communications made from the VoIP phones 116, 118, and 120 or other telecommunications devices in the locations 110, 112, and 114 is tracked, recorded, and later invoiced by the billing database 106. As a result, the patient may use any of the telecommunications devices within the locations 110, 112, and 114 to communicate during a stay at the medical facility without any undue hardship or inconvenience.

For example, the patient may have undergone a difficult surgery for cancer and as a result may have temporarily lost mobility. By tracking the presence of the patients through the locations 110, 112, and 114, the patient may be able to use the previously established account to make and receive phone calls through any of the VoIP phones 116, 118, and 120. The patient may not be required to request assistance or leave his or her bed in order to retrieve a cell phone or credit card for making a call from the VoIP phones 116, 118, and 120. Any telecommunications charges incurred from the location 110, 112, and 114 corresponding to the patient's presence may be automatically recorded or billed to the patient by the billing database 106.

Any other communications made from the locations 110, 112, and 114, may similarly be tracked for billing purposes. Other communications or communications related expenses may include surfing the internet, e-mail or text messages, electronic greeting cards, faxes, scans or other office work, and television related purchases, such as renting movies or a view-on-demand or pay-for-view presentation. The communications received by the patient at any of the locations 110, 112, and 114 may be sent through the communications management system 102 and hospital communications network 108 through the communications network 124.

The communications network 124 may represent any number of networks and communications service providers that may be interconnected to send and receive communications. In particular, the client 128, the cell phone 126, and the VoIP phone 122 are shown as simplified examples of devices, systems or patients that may communicate with the patient through the communications management system 102 at the corresponding locations 110, 112, and 114. Despite the inconvenience of entering or visiting a hospital, the patient may still have access to communications typically available through the patient's home, business, library or other similarly used facility.

The illustrative embodiments, may allow a patient to be contacted in any of the locations 110, 112, and 114 or within the applicable facility using a single phone number, user name, account number, email address, web address or other assigned contact information. In one embodiment, a single phone number assigned to the user may allow friends and family to call the patient. As a result, individuals trying to contact the patient do not have to worry about multiple phone numbers, speaking with an operator each time or bothering other patients during the patient's stay at the facility. The phone number dialed may automatically ring or connect to a device in location of the patient. In one embodiment, the communications management system 102 or server 104 may be equipped with a voicemail server. The server 104 may automatically transfer a voicemail account to a new location. Similarly, preferences or programming, such as temporary speed dial numbers and call screening information, may be automatically transferred to the new telecommunications devices. For example, when the patient moves from location 110 to location 114, the screening preferences that automatically sends calls from the patient's mother-in-law to voicemail from the VoIP phone 116 are similarly implemented on the VoIP phone 120. Any number of programmable features, services or settings may be transferred between telecommunications devices, and elements of the locations 110, 112, and 114 based on the detected presence of the patient.

Figure 2:
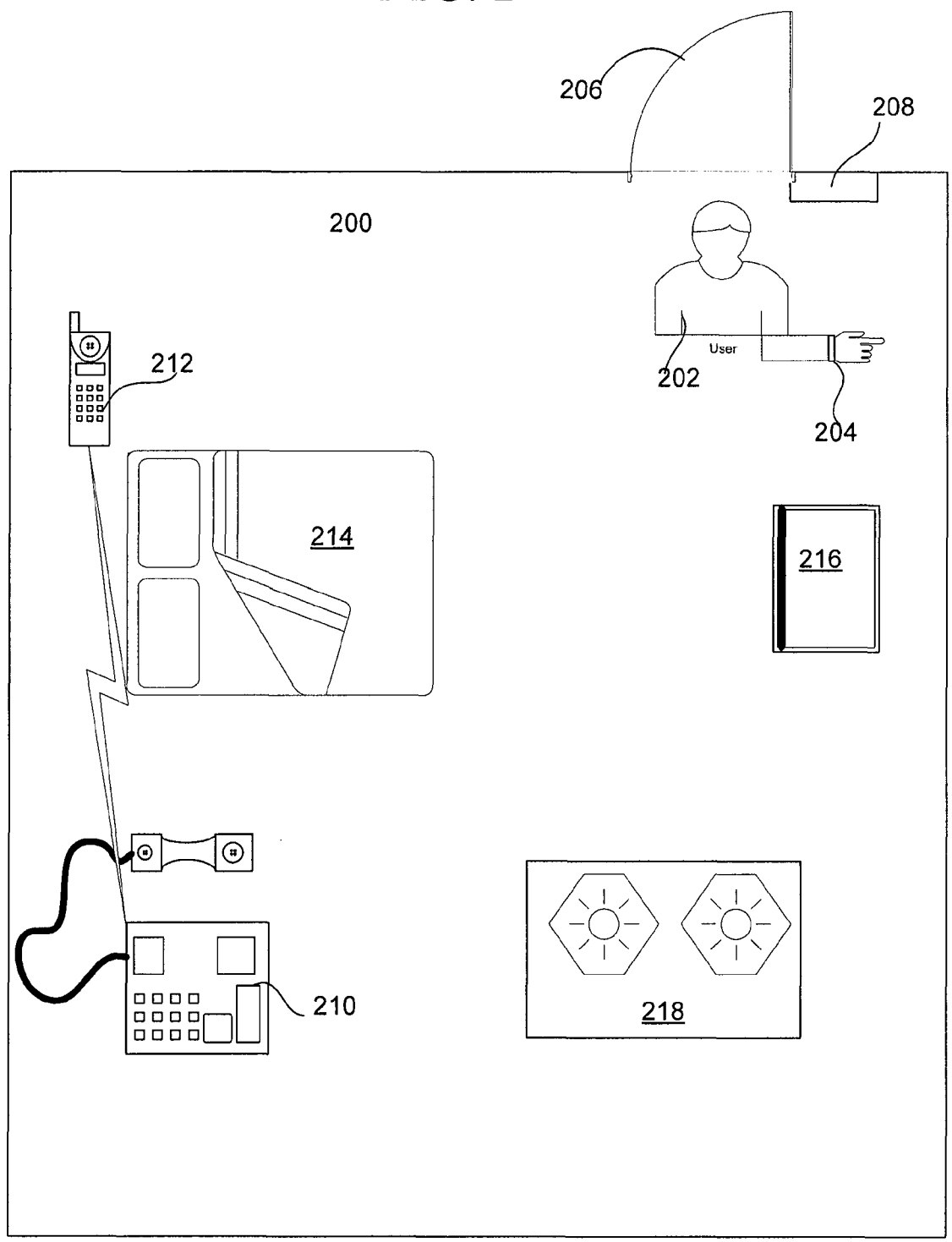
FIG. 2 is a pictorial representation of a location within a hospital in accordance with an illustrative embodiment.

FIG. 2 is a pictorial representation of a location within a hospital in accordance with an illustrative embodiment. The location 200 is a particular implementation of any of the locations 110, 112, and 114 of FIG. 1. The location 200 may include numerous devices, furniture and other elements. In one embodiment, the location 200 may include a patient 202 wearing an identifier 204, an entrance 206, a scanner 208, a VoIP phone 210, a cordless handset 212, a bed 214, a television 216, and lights 218.

As shown in FIG. 2, the location 200 may be a hospital room of the patient 202. The patient 202 represents one or more patients assigned to the location 200 or visiting the medical facility as a group. For example, the patient 202 may also include a spouse, companion, friend, one or more children or other individuals that are collectively visiting the location 200. The patient 202 may be assigned the identifier 204. In FIG. 2, the identifier is shown as a medical bracelet. The identifier may include or store information associated with the patient 202, and in particular, may be used to determine the presence of the patient 202 in the location 200.

The location 200 may include the entrance 206. The entrance 206 is an ingress or egress location to the location 200. In one embodiment, the location 200 may not have an entrance 206 or may have multiple entrances. In one embodiment, the scanner 208 may be positioned at or near the entrance 206. The scanner is a device configured to detect the presence of the patient 202 based on the identifier 204. In one embodiment, the identifier 204 may be equipped with a radio frequency identification (RFID) tag. The scanner 208 may be a RFID tag reader that detects each time the patient 202 and corresponding identifier 204 enters or leaves the location 200. The scanner 208 may automatically detect the presence of the patient 202 based on the identifier without the patient 202 taking any affirmative actions. In another embodiment, the identifier 204 may include a bar code, account number or password that may be manually entered or read by the scanner 208. For example, the scanner 208 may include a laser scanner for reading a bar code from the identifier 204. The patient 202 or other authorized personnel may assist the patient 202 in scanning the identifier 204 each time the patient 202 enters or leaves the location 200. For example, in the event the patient 202 is partially paralyzed, medical staff may assist the patient 202 in scanning the identifier 204 each time the patient 202 enters or leaves through the entrance 206.

The scanner 208 may be a battery powered or built-in system that communicates with a server, database or other portion of the communications management system. In one embodiment, the scanner 208 may communicate with a communications management system through an Ethernet connection. In another embodiment, the scanner 208 may be battery powered and may wirelessly communicate with the communications management system using a standard or protocol, such as IEEE 802.11(n), WiMAX, Bluetooth or other suitable short range wireless communications standards.

In one embodiment, the scanner 208 may be integrated with the VoIP phone 210, the handset 212, the bed 214, a remote control or other device or element within the location 200. For example, the scanner 208 may be integrated with the VoIP phone 210 so that any time the patient 202 reaches to make a phone call through the VoIP phone 210 or the handset 212, the identifier 204 is detected by the scanner 208 within the VoIP phone 210. As a result, the phone call is associated with a temporary account of the patient 202 and the location 200.

The identifier 204 may also be linked or associated with environmental conditions and information of the patient 202. The environmental conditions are the settings and configuration of the functional elements within the location 200. In one embodiment, the amenities, furniture, medical equipment or the devices of the location 200 may be remotely configured based on the patient 202 entering the location 200. For example, the bed 214 may be reconfigured to a last used position. The television 216 may be changed to a preferred channel or may implement previously defined filtering information. Similarly, the lights 218 may be dimmed, brightened or otherwise configured based on preferences of the patient 202 or based on the needs or medical requirements of the patient 202 as entered or noted by staff through the communications management system. In one embodiment, the temperature of the location 200 may also be reconfigured based on the entrance or exit of the patient 202 as detected by the scanner 208. For example, using a laptop available from a nursing station, a nurse may indicate that the patient 202 is hard of hearing and as a result, the volume on the television 216 has a default level substantially higher than normal. In other words, the environmental conditions of the location 200 may be configured to change or pre-configure themselves based on the entry of the patient 202 in the location 200 as detected by the identifier 204.

Information associated with the patient 202 may also be displayed to one or more displays in the location 200. For example, each time a staff member from the hospital enters the location 200, a similar identifier utilized by the staff member may be detected by the scanner 208. As a result, the patient information may be displayed to one or more displays that may include the television 216 and the VoIP phone 210. For example, the patient information may indicate any known allergic reactions, patient history, charts, procedures, needs or other information that may assist the individual in carrying for, helping or otherwise serving the patient 202.

In another embodiment, the identifier 204 may be a code printed or embedded in a medical bracelet that the patient 202 may enter into the VoIP phone 210 upon being assigned or admitted to the location 200. As a result, the patient 202 may be required to take an affirmative action in order to indicate the patient's presence in the location 200. By registering the information available from the identifier 204, the patient 202 may link a temporary account in order to make and receive phone calls from the VoIP phone 210, surf the Internet through a computing system connected to the television 216 order entertainment through the television 216 or otherwise communicate with individuals internal or external to the medical facility.

The VoIP phone 210 and the handset 212 may function as a single communications device. In one embodiment, the handset 212 communicates with the VoIP phone 210 through a short range frequency that is acceptable based on the medical equipment, devices or other elements that may be sensitive to radio frequencies within the location 200. The handset 212 may be beneficial because it may allow the patient 202 to utilize the handset 212 and VoIP phone 210 from anywhere within the location 200 unlike the VoIP phone 210 which may be fixed or have movement limitations based on a cord or other hardware configuration. In one embodiment, the patient may configure the handset 212 or the VoIP phone 210 or may use a remote control, keyboard, mouse or other interface to the telecommunications devices of the location 200 to direct all incoming communications into a queue or a voicemail system that may be retrieved at a later time. As a result, the patient 202 or administrative staff, doctors or others may ensure that the patient is able to rest or have a reprieve from incoming communications. For example, if the patient 202 needs to take a shower, the VoIP phone 210 and other telecommunications device may be configured to temporarily send all calls to a queue or voicemail.

The account that is temporarily or permanently assigned to the patient 202 may similarly be linked with a temporary e-mail account, website, wild or other communication elements configured to allow the patient 202 to receive both internal or external communications. Each of the services may be provided and managed by the communications management system of the facility or a third-party provider. For example, a temporary e-mail account and wireless keyboard accessible from the bed 214 may allow the patient 202 to receive and send electronic messages which may be displayed on the television 216. Similarly, well wishers may send electronic greeting cards or other messages through a website or portal linked with the communications management system.

In another embodiment, a wireless device, such as a facility-authorized cell phone, remote control or wireless keyboard may enable the patient 202 to send e-mail, text messages or otherwise wirelessly communicate through the VoIP phone 210 or through a separate wireless network connection.

Figure 3:
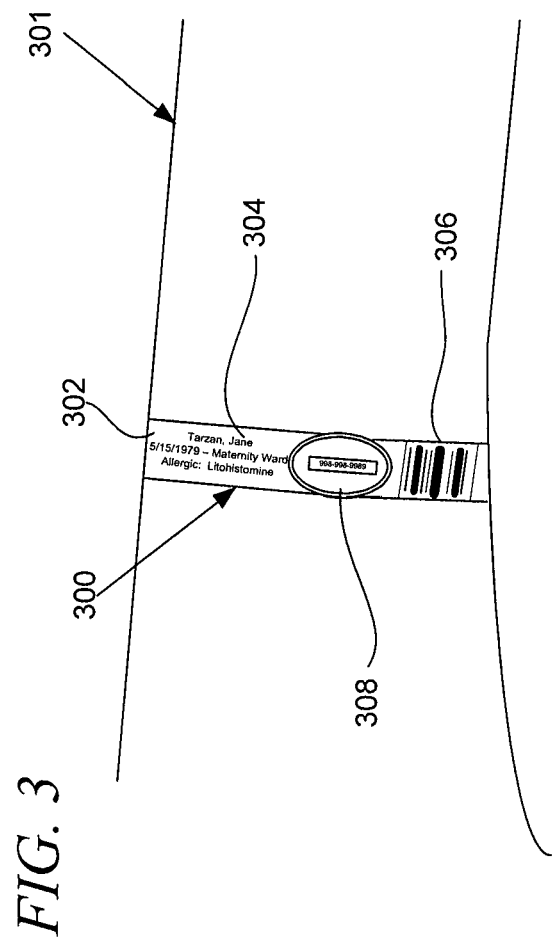
FIG. 3 is a pictorial representation of a bracelet for use in a hospital in accordance with an illustrative embodiment.

FIG. 3 is a pictorial representation of a bracelet for use in a hospital in accordance with an illustrative embodiment. The bracelet 300 is a particular implementation of the identifier 204 of FIG. 2 that may be secured to a wrist 301 of a patient. In one embodiment, the bracelet may include a strap 302, patient information 304, a bar code 306, and a RFID tag 308.

FIG. 3 illustrates a bracelet 300 that may be worn on the wrist 301 of a patient. In another embodiment, the bracelet 300 may be replaced by a card, token, ring, patch or information that may be secured to or worn by the patient. In other embodiments, the bracelet 300 may be worn as a name tag, necklace, anklet or article of clothing. The type of bracelet 300 or identifier utilized for the patient may depend on the circumstances, needs or medical condition of the patient. The bracelet 300 is useful because many patients are accustomed to wearing a temporary bracelet or identifier when checking into a medical facility for themselves or when visiting someone they are associated with. As shown, the bracelet 300 may include patient information 304. The patient information 304 is data and information for the patient. In particular, the patient information 304 may include a name, check-in date, allergies, assigned building, known conditions or other important or relevant medical information. The patient information 304 may be written on the bracelet 300 or stored in the RFID tag for secure retrieval by authorized personnel.

The bracelet 300 may also include the RFID tag 308. The RFID tag is a device that may be scanned or read by an RFID reader whenever the patient approaches within a specified proximity of the reader. The RFID tag 308 may be a passive device that is read by the reader by reflecting a signal or temporarily activating circuitry. Alternatively, the RFID tag 308 may be an active device that actively broadcasts a signal, such as patient information and preferred environmental conditions, at all times or when activated. For example, the RFID tag 308 may be read anytime the patient enters or exits a door. The RFID tag 308 may be used to determine the presence or current location of the patient.

In another embodiment, the RFID tag 308 may be used to determine information critical for the care or well being of the patient. For example, the RFID tag 308 may determine how many times the patient entered a bathroom of the patient's room during the night. Similarly, the RFID tag 308 may be used to determine whether the patient was responsive to instructions to walk the hallway or otherwise obtain exercise, visit the cafeteria or otherwise perform a specified movement or action detectable by the RFID tag 308.

In one embodiment, the bracelet 300 may also include a bar code 306. The bar code 306 may be scanned when a patient enters or leaves each of multiple locations. In one embodiment, the patient may be required to hold the bracelet 300 to a bar code reader in order to enter a location. The bracelet 300 may be used to not only track the presence of the patient, but also grant authorization to enter specified portions of the facility. For example, the patient may be able to enter a nursery only if the information associated with the bracelet 300 indicates that the patient has been granted authorization. Similarly, the RFID tag 308 or the bar code 306 may be utilized to purchase communication services as previously described order meals or otherwise pay for or request services needed by the patient.

In one embodiment, the bracelet 300 ensures that communications intended for the patient are routed to the current location of the patient regardless of how many locations the patient has visited or based on the past locations of the patient. The presence of the patient may be determined using the RFID tag 308, bar code 306, code or any combination thereof integrated as part of the bracelet.

Figure 4:
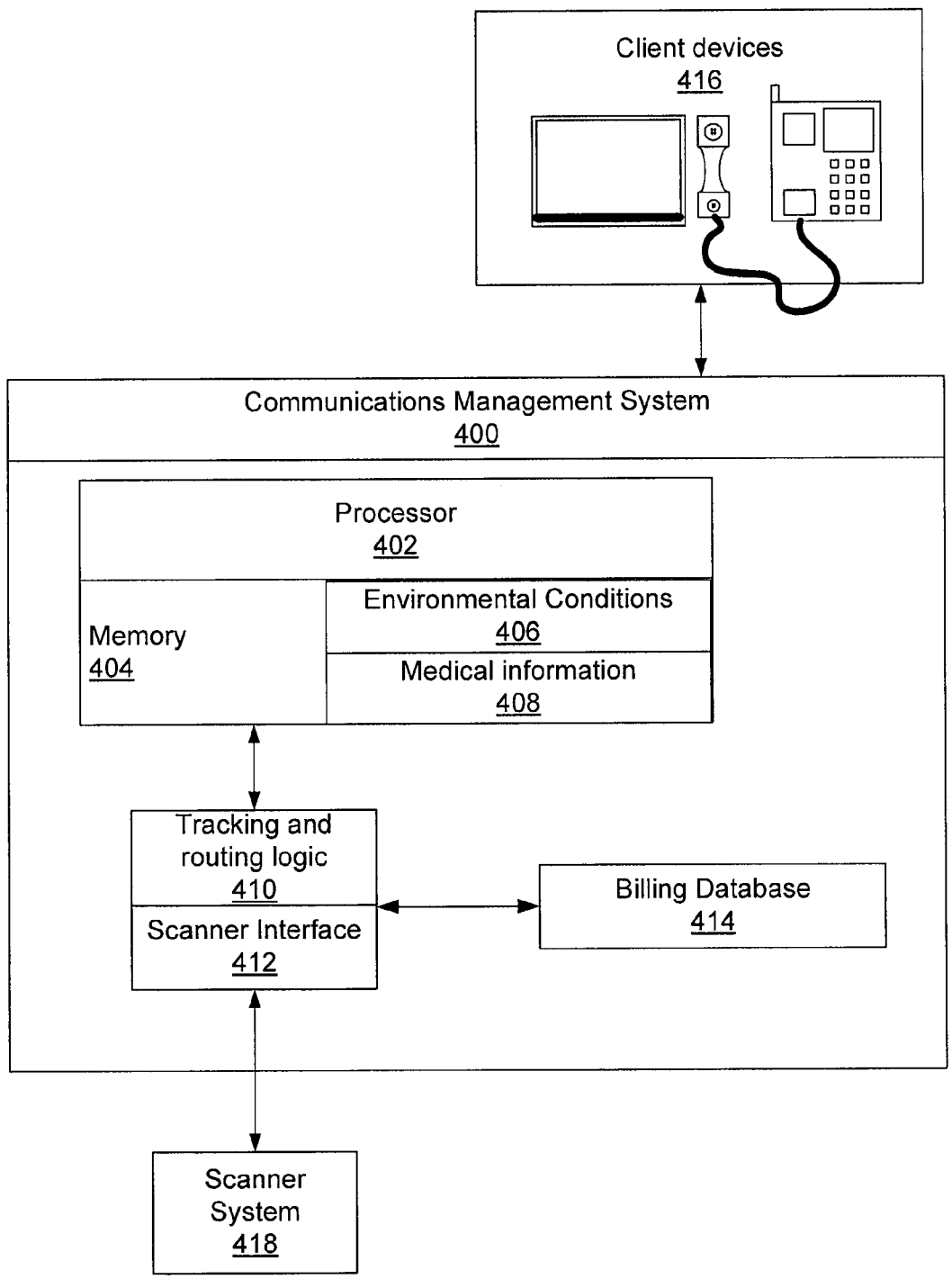
FIG. 4 is a block diagram of a communications management system in accordance with an illustrative embodiment.

FIG. 4 is a block diagram of a communications management system in accordance with an illustrative embodiment. The communications management system 400 may include any number of hardware and software components, cards, devices, and elements. In one embodiment, the communications management system 400 may include a processor 402, a memory 404, environmental conditions 406, medical information 408, tracking and routing logic 410, scanner interface 412, and a billing database 414. The communications management system 400 may further communicate with any number of devices, patients or components which may include client devices 416 and scanner system 418. The communications management system 400 is a particular implementation of the communications management system 102 of FIG. 1.

The processor 402 is circuitry or logic enabled to control execution of a set of instructions. The processor 402 may be a microprocessor, digital signal processor, central processing unit or other device suitable for controlling an electronic device including one or more hardware and software elements, executing software, instructions, programs and applications, converting, and processing signals and information, and performing other related tasks. The processor 402 may be a single chip or integrated with other computing or communications elements.

The memory 404 is a hardware element, device or recording media configured to store data for subsequent retrieval or access at a later time. The memory 404 may be static or dynamic memory. The memory 404 may include a hard disk, random access memory, cache, removable media drive, mass storage or configuration suitable as storage for data, instructions, and information. In one embodiment, the memory 404 and processor 402 may be integrated. The memory may use any type of volatile or non-volatile storage techniques and mediums.

The memory 404 may further store the environmental conditions 406 and the medical information 408. The environmental conditions 406 is the preferred settings and configuration for telecommunications devices, media equipment, medical devices, furniture, and other configurable elements at the patient's location. The environmental conditions 406 may include information regarding temperature, settings and configurations of a bed, media preferences, such as preferred channels and allowed content, speed dial numbers, and other similar information. The medical information 408 is information related to the treatment or stay of the patient at the location. The medical information 408 may include name, address, chart, patient history, diagnosis, prescribed drugs, allergies or other information related to the patient's care or wellbeing during a visitor's stay at the location.

In one embodiment, the medical information 408 may include allergies and diagnosis information that are automatically displayed to a monitor or television within the patient's location when authorized personnel are detected within the location. For example, if a nurse enters the room wearing an RFID tag indicating that she is authorized to view the medical information 408, the medical information 408 may be streamed, displayed or output to a device within the location.

In one embodiment, the other elements of the communications management system 400 may also be stored as instructions in the memory 404 for execution by the processor 402. The tracking and routing logic 410, the scanner interface 412, and the billing database 414 may be hardware, software or a combination of both, that implement the features, services, and methods herein described.

The tracking and routing logic 410 is the logic configured to detect the presence and current location of the patient. The tracking and routing logic 410 may route communications through any number of intermediary devices in order to ensure the patient is able to make and receive communications, such as a phone call. In one embodiment, the tracking and routing logic 410 may register the current location of the patient with another router, server, switch or device configured to send and receive communications associated with the patient. For example, the patient may have a virtual phone number assigned at the time the patient initiates the visit at the location. As a result, all incoming communications to the virtual phone number are routed to the current location of the patient.

The scanner interface 412 is an interface configured to determine the presence or location of the patient based on information from the scanner system 418. The scanner system 418 is one or more scanners, detectors or electronic readers configured to determine the location of a patient based on an identifier. The scanner system 418 may be a collection of any number of devices in a network to communicate with the scanner interface 412. In one embodiment, the scanner system 418 is a hardwired configuration of RFID readers that communicate with the scanner interface 412 through an Ethernet network. In another embodiment, the scanner system 418 may be a bar code readers enabled through a wireless network of the facility. In yet another embodiment, the scanner system 418 may be an attachment or programming for a network of VoIP phones that detects the presence of a patient based on an assigned indicator. Similarly, other suitable communications mediums, lines or services may be utilized to propagate communication between the scanner system 418 and the scanner interface 412.

The billing database 414 is a structured collection of records or data configured to store information relating to expenses incurred by the patient. In one embodiment, the billing database 414 may track the utilization of communication services provided by the hospital or a communications service provider serving the hospital or medical facility. For example, any time the patient makes a call from one or more locations, the call may be billed, recorded or logged to the patient's account for immediate or subsequent payment. In one embodiment, expenses incurred by the patient may require that the billing database 414 immediately receive payment from the patient through a credit card account or other payment scheme. For example, in order to view a pay-per-view movie, the billing database 414 may charge a credit card associated with the patient to ensure that expenses are carefully tracked and charges are sent and received as incurred by the patient.

In one embodiment, the billing database 414 tracks utilization of the client devices 416 by the patient. As previously described, the client devices may include a VoIP phone, wireless device, computing system, television, fax machine or other communication elements available from the current location of the patient. The billing database 414 may be part of or networked to one or more other databases, such as databases for patient information and preferred environmental conditions.

Figure 5:
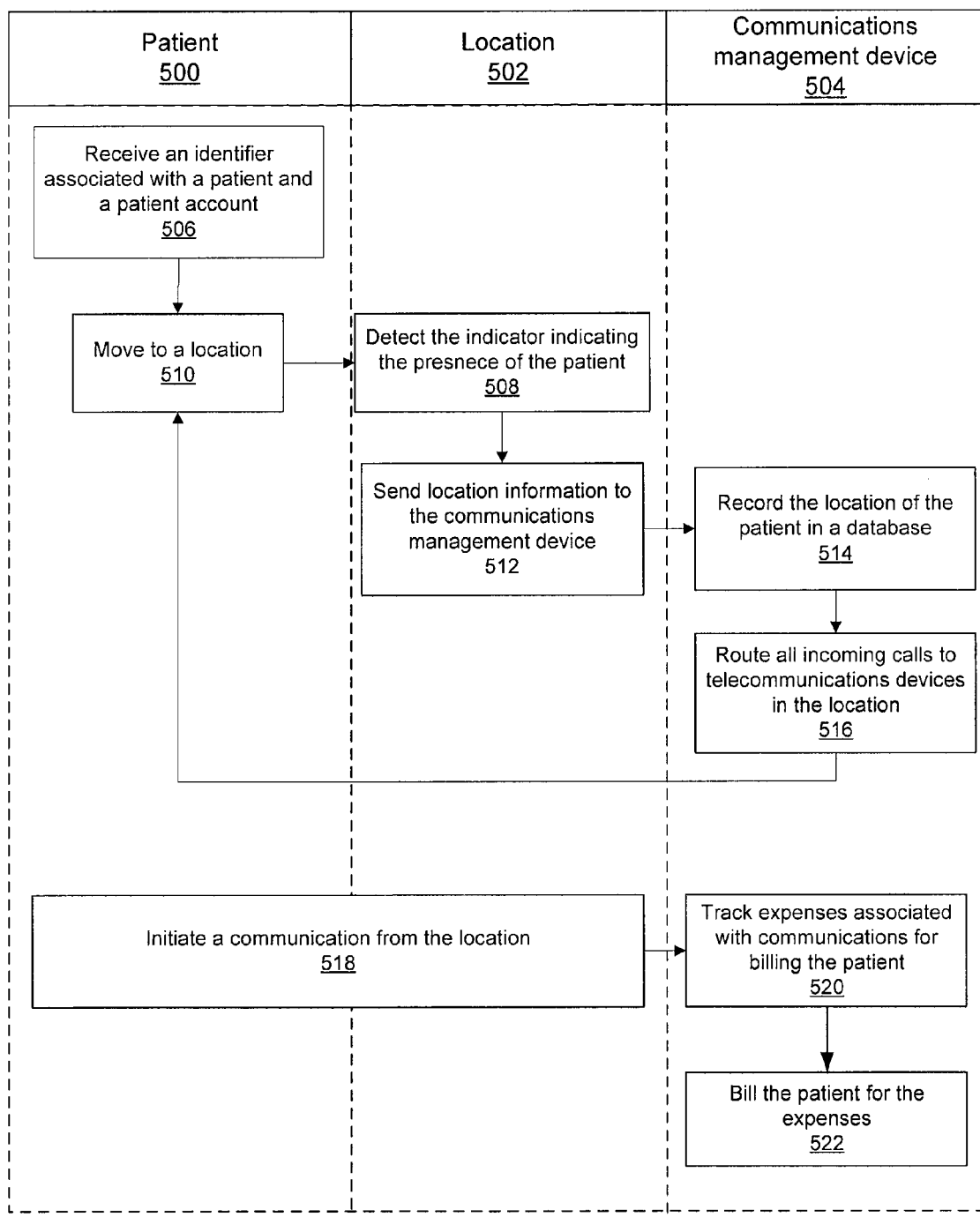
FIG. 5 is a flowchart of a process for routing communications to a patient in accordance with an illustrative embodiment.

FIG. 5 is a flowchart of a process for routing communications to a patient in accordance with an illustrative embodiment. The process of FIG. 5 may be implemented by a patient 500, a location 502, and a communications management system 504. The process may be initiated by receiving an identifier associated with the patient and a patient account (step 506). The identifier may be a medical bracelet, dog tag, name tag, token, sticker or device suitable for use in the location 502.

In one embodiment, the patient 500 may be required to register with the medical facility or service provider operating the location 502. The patient and the patient account may be linked with a virtual phone number, e-mail address, website, chat name or other information that may be used to communicate with the patient 500 during a stay at the medical facility. As a result, the patient 500 may always be able to communicate regardless of how many times the patient moves rooms or locations within the facility.

Next, the patient 500 moves to a location (step 508). The patient 500 may move based on his or her own volition or may be required to move as part of treatment. The location 502 detects the identifier indicating the presence of the patient (step 510). The identifier may be a RFID tag, bar code, wireless transmitter or other broadcast element or information that indicates the presence of the patient and the location 502. The location 502 sends location information to the communications management system (step 512).

Next, the communications management system 504 records the location of the patient 500 in a database (step 514). The location of the patient 500 may be updated, reconfigured or otherwise saved in a file, field or other information of the database.

Next, the communications management system 504 routes all incoming communications to the telecommunications devices at the location (step 516). The incoming communications may include phone calls, e-mails or text messages, instant chat sessions, website updates, RSS feeds or other messages or forms of communications received by one or more of the telecommunications devices at the location 502. During step 516, the settings, preferences, and programming is transferred to the telecommunications devices at the location. For example, voicemail configuration, call blocking, speed dial numbers, soft key configuration, bed settings, preferred phone numbers, day and night temperature, lighting intensity, and messaging alerts may be setup and configured at the new location.

Each time the patient 500 moves a location (step 508), the location 502 similarly detects the identifier indicating the presence of the patient (step 510). As a result, the location 502 sends the location information to the communications management device (step 512) in order to update the database of the communications management system 504. Similarly, at any time the patient 500 may initiate a communication from the location (step 518). The communication may be initiated by utilizing the telecommunications devices enabled or provided at the location 502. The communications management system 504 tracks expenses associated with communications for billing the patient (step 520). Only communications with present expenses may be charged to the patient. For example, an agreement signed by the patient 500 when signing in to the facility may indicate that local phone calls are not charged to the patient 500. Similarly, the patient 500 may be allotted a preset number of long distance minutes, e-mails, text messages or Internet surfing as part of the patient's stay at the location 502.

Next the communications management system 504 bills the patient 500 for the expenses (step 522). The patient may be billed at a specified interval or based on an event. For example, each time a bill associated with the patient reaches $50.00 the patient's credit card may be billed or in another embodiment, the patient may be billed each time a present threshold is met, such as, phone calls or Internet usage for more than 200 minutes.

FIG. 6 is a pictorial representation of a billing invoice in accordance with an illustrative embodiment. The billing invoice 600 may include a name 602, date 604, payment information 606, charges 608, total 610, and phone record 612. The billing invoice 600 is an example of a record tracking telecommunications usage by a patient. The billing invoice 600 may also be integrated with a bill, invoice or other expense record sent to the patient by the hospital or applicable service provider. For example, the billing invoice 600 may also include expenses for procedures performed, lab tests, service costs, drugs, applicable taxes and fees, cafeteria expenses, and other expenses incurred by the patient or charged by the facility. The name 602 lists the name or names of the patient. The date 604 indicates the time period during which the patient was at the facility. For example, the listed patient may have been at the facility for four days. The payment information 606 may specify how the patient is billed for expenses incurred.

In one embodiment, a credit card of the patient may be billed. In another embodiment, the billing invoice 600 may be sent directly to the client. In yet another embodiment, the account balance may be added to an existing balance charged to the patient.

The charges 608 specify the communications or media services utilized by the patient during the date 604. The charges 608 may provide a detailed record or summary of communications and services utilized by the patient. For example, the patient may have viewed any number of movie-on-demand or pay-per-view presentations, utilized Internet access, sent e-mail, chat or send text messages, and made outgoing phone calls.

The total 610 is the addition of all of the charges incurred for the patient. The phone record 612 may specify the numbers or devices called by the patient. The phone record may also list a date and charge similar to a bill typically provided by a communication service provider. The phone record may also show charges per minute, location from which the call was made, and other information that may help the patient remember when each of the phone calls was made.

The illustrative embodiments provide a system and method for enhancing communications and convenience of a user in a facility. In one embodiment, the user is a patient is a medical facility that may benefit from dynamic routing of communications and customization of devices, software, and other elements within the patient's room. A single set of communications information, such as a virtual phone number, temporary email address, username or web address may allow multiple parties to communicate with the patient. As a result, the patient may select to receive, delay, block or otherwise send and receive communications at the patient's convenience and based on the current circumstances.

The previous detailed description is of a small number of embodiments for implementing the invention and is not intended to be limiting in scope. The following claims set forth a number of the embodiments of the invention disclosed with greater particularity.

What is claimed is:

1. A method for tracking a person at a facility to enable communications, the method comprising:
   assigning, to the person at the facility, a telephone number for routing communications to the person while at the facility;
   automatically detecting, for communication management, a presence of the person at a location, from a plurality of locations within a facility, as the person moves throughout the facility, without interaction from the person, the detecting comprising scanning an identifier comprising a radio frequency identification (RFID) tag assigned to the person;
   storing information, with a computer, about the location of the person in a database, the storing comprising updating a profile of the person to designate the location as a current location of the person for managing communications intended for the person;
   automatically associating, with a computer, communications intended for the person with the location, wherein automatically associating the communications intended for the person with the location comprises associating the telephone number with a voice over Internet Protocol ("VoIP") telephone at the location;
   automatically transferring one or more individualized user settings associated with the person to the VoIP telephone at the location; and
   automatically routing, with the computer, the communications to a telecommunications device located at the location, based on associating the communications with the location.

2. The method according to claim 1, wherein the telecommunications device includes one or more of a computing device and a communications device, and wherein the profile comprises one or more communications identifiers selected from the group consisting of a phone number, an email address, a uniform resource locator ("URL") of a website, and a username.

3. The method according to claim 1, wherein the RFID tag is incorporated in a bracelet.

4. The method according to claim 1, further comprising:
   associating environmental conditions with the location.

5. The method according to claim 4, further comprising:
   configuring the location to meet the environmental conditions in response to updating the profile to designate the location as a current location.

6. The method according to claim 4, wherein the environmental conditions include any of lighting, temperature, configuration of a bed, and entertainment options.

7. The method according to claim 1, wherein the person is a patient in a medical facility, the method further comprising:
   configuring one or more displays at the location to display medical information about the person.

8. The method according to claim 7, further comprising:
   displaying the medical information to authorized personnel at the location.

9. The method according to claim 8, wherein the displaying is performed in response to detecting an identifier associated with the authorized personnel.

10. The method according to claim 1, further comprising: rerouting the communications to a new location, in response to detecting the person at the new location.

11. The method according to claim 1, further comprising: billing the person for communications made from the one or more telecommunications devices.

12. The method according to claim 1, wherein the location is a room within the facility.

13. The method according to claim 1, wherein the facility is a medical facility.

14. The method according to claim 1, further comprising: displaying the communications on a television at the location.

15. The method according to claim 1, wherein automatically detecting a presence of a person further comprises: scanning, at the location, a bar code associated with the person.

16. The method according to claim 1, wherein the communications comprise a voice over Internet Protocol ("VoIP") communication.

17. A server for routing communications to a person at a facility, the server comprising:
a communications interface configured to receive an input from one or more radio frequency identification (RFID) scanners configured to scan an identifier comprising an RFID tag assigned to the person, the input specifying an automatically detected presence of the person at a location, from a plurality of locations within a facility, as the person moves throughout the facility, based on locations of the one or more RFID scanners and the identifier;
a processor;
logic to program the processor to assign, to the person at the facility, a telephone number for routing communications to the person while at the facility;
logic to program the processor to store information about the location of the person in a database, including logic to program the processor to update a profile of the person to designate the location as a current location of the person for managing communications intended for the person;
logic to program the processor to automatically associate communications intended for the person with the location, wherein automatically associating the communications intended for the person with the location comprises associating the telephone number with a voice over Internet Protocol ("VoIP") telephone at the location;
logic to program the processor to automatically transfer one or more individualized user settings associated with the person to the VoIP telephone at the location; and
logic to program the processor to automatically route the communications to a telecommunications device located at the location in response, based on associating the communications with the location.

18. The system according to claim 17, wherein the server further comprises a memory for storing environmental conditions associated with the person, wherein the room is configured to meet the environmental conditions response to detecting the presence of the person in the room.

19. A non-transitory computer readable medium encoded with logic to program a processor of computer to route communications to a person at a facility, the logic comprising:
logic to program the processor to assign, to the person at the facility, a telephone number for routing communications to the person while at the facility;
logic to program the processor to receive an input from one or more radio frequency identification (RFID) scanners configured to scan an identifier comprising an RFID tag assigned to the person, the input specifying an automatically detected presence of the person at a location, from a plurality of locations within a facility, as the person moves throughout the facility, based on locations of the one or more RFID scanners and the identifier;
logic to program the processor to store information about the location of the person in a database, including logic to program the processor to update a profile of the person to designate the location as a current location of the person for managing communications intended for the person;
logic to program the processor to automatically associate communications intended for the person with the location, wherein automatically associating the communications intended for the person with the location comprises associating the telephone number with a voice over Internet Protocol ("VoIP") telephone at the location;
logic to program the processor to automatically transfer one or more individualized user settings associated with the person to the VoIP telephone at the location; and
logic to program the processor to automatically route the communications to a telecommunications device located at the location in response, based on associating the communications with the location.

20. The method of claim 1, wherein the one or more individualized user settings comprise one or more settings selected from the group consisting of voicemail configuration, call blocking settings, speed dial numbers, and soft key configuration.

* * * * *